United States Patent [19]

Clauss et al.

[11] Patent Number: 5,438,071
[45] Date of Patent: Aug. 1, 1995

[54] STABLE PORFIMER SODIUM COMPOSITIONS AND METHODS FOR THEIR MANUFACTURE

[75] Inventors: Steven L. Clauss, Manville, N.J.; Michael J. Pastel, Highland Mills, N.Y.; Rainer K. Zawadzki, Wuhan, China

[73] Assignee: American Cyanamid Company, Stamford, Conn.

[21] Appl. No.: 75,227

[22] Filed: Jun. 10, 1993

Related U.S. Application Data

[62] Division of Ser. No. 873,860, Apr. 27, 1992, Pat. No. 5,244,914.

[51] Int. Cl.$^6$ .............................................. A61K 31/40
[52] U.S. Cl. ..................................... 514/410; 540/145
[58] Field of Search ......................... 514/410; 540/145

[56] References Cited

U.S. PATENT DOCUMENTS

| | | | |
|---|---|---|---|
| 4,649,151 | 3/1987 | Dougherty et al. | 514/410 |
| 4,861,876 | 8/1989 | Kessel | 540/145 |
| 4,882,234 | 11/1989 | Lai et al. | 514/185 |
| 5,028,621 | 7/1991 | Dougherty et al. | 514/410 |
| 5,059,619 | 10/1991 | Haeger et al. | 514/410 |

FOREIGN PATENT DOCUMENTS 44-14334  6/1969  Japan .

OTHER PUBLICATIONS

Patent Abstracts of Japan, vol. 11, No. 262 (1987) and JP-A-62 063 586.
Patent Abstracts of Japan, vol. 11, No. 096 (1987) and JP-A-61 246 232.
Bonnett et al., *HPD—A Study of its Components and Their Properties*, 160 Adv. Exp. Biol. Med. 241–50 (1983).
Kessel et al., *Probing the Structure and Stability of the Tumor-localizing Derivative of Hematoporphyrin by Reductive Cleavage with LiAlH₄*, 47 Cancer Research 4642–45 (1987).
Lipson et al., *The Use of a Derivative of Hematoporphyrin in Tumor Detection*, 26 J. Natl. Cancer Inst. 1–8 (1961).
Barry et al., *Organic Syntheses without Solvent: Base-catalysed Ester Interchange*, 29 Tetrahedron Letters 4567–68 (1988).
Pandey et al., *Syntheses and Photosensitizing Activity of Prophyrins Joined with Ester Linkages*, 49 Cancer Research 2042–47 (1989).
Dougherty et al., *Photoradiation Therapy for the Treatment of Malignant Tumors*, 38 Cancer Research 2628–35 (1978).
Dougherty et al., *Photoradiation in the Treatment of Recurrent Breast Carcinoma*, 62 Natl. Cancer Inst. 231–37 (1979).
Morris et al., *The Synthesis of Dihematoporphyrin Ether and Related Porphyrin Dimers*, 29 Tetrahedron Letters, 2501–2504 (1988).
Banerjee et al., *A Simple One-step Synthesis of Phenyl Ethers from Phenyl Acetates*, 1982 J. Chem. Soc., Chem. Commun. 815–16 (1982).
Pass et al., *Photodynamic Therapy*, 9 Mediguide ® to Oncology 1–8 (P. Wiernik ed. 1989).

*Primary Examiner*—Peter O'Sullivan
*Assistant Examiner*—Brian M. Burn
*Attorney, Agent, or Firm*—Morrison & Foerster

[57] ABSTRACT

A storage stable porfimer sodium (polyhematoporphyrin ether/ester) composition useful in the photodynamic therapy of cancer and other conditions is provided. The composition is characterized in that the percentage of ester linked porphyrin oligomers is less than 10% of the composition. Improved processes for preparing such compositions are also provided wherein acetylated hematoporphyrin is treated with alkali for sufficient time and temperature to reduce the amount of porphyrin oligomers joined by ester linkages to less than 10% of the composition.

7 Claims, 2 Drawing Sheets

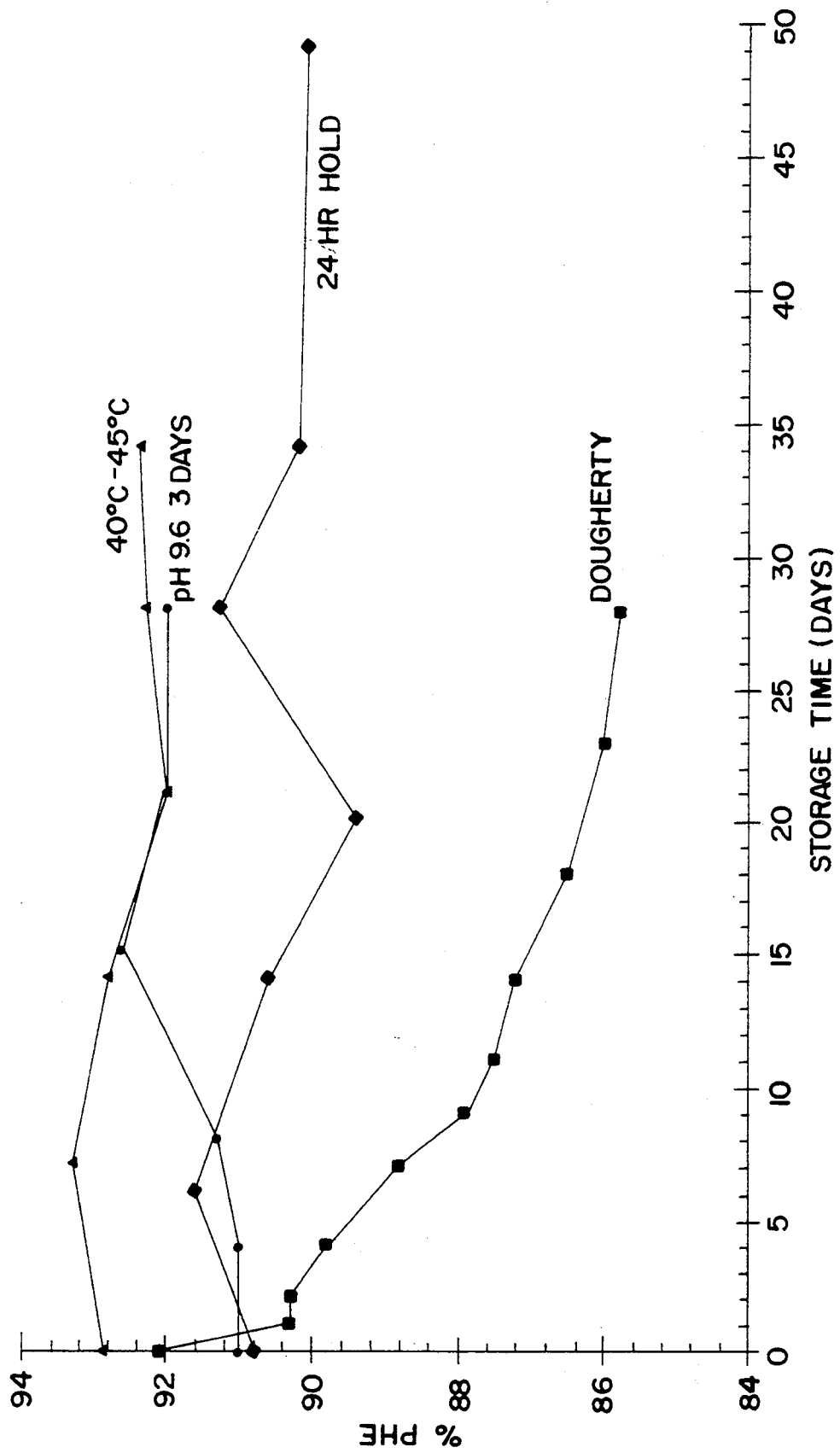

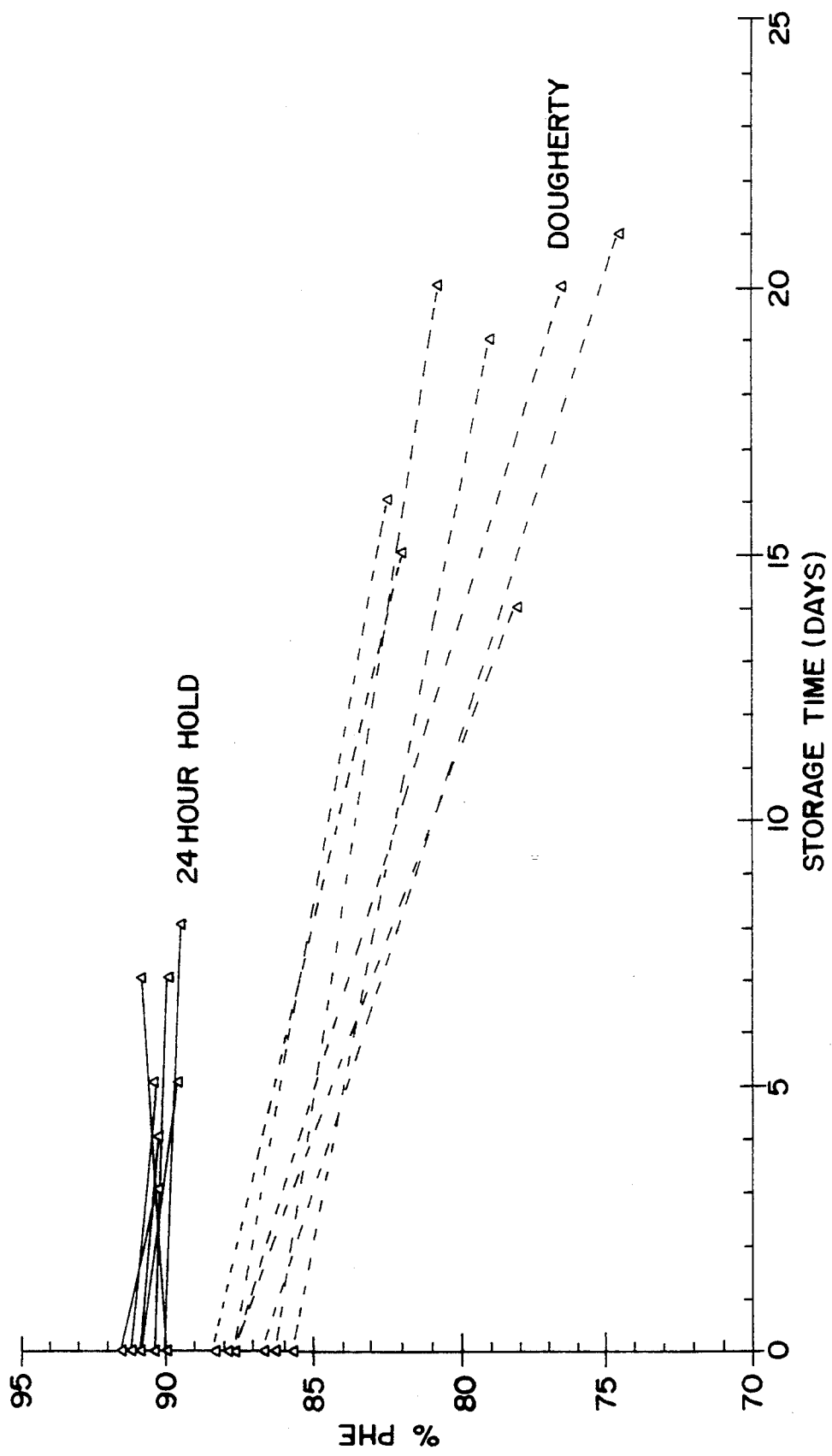

STABLE PORFIMER SODIUM COMPOSITIONS AND METHODS FOR THEIR MANUFACTURE

This application is a division of application Ser. No. 07/873,860 filed, Apr. 27, 1992 (now U.S. Pat. No. 5,244,914).

BACKGROUND OF THE INVENTION

1. Field of the Invention

The invention relates to storage stable porfimer sodium compositions useful in photodynamic therapy and improved methods for their manufacture.

2. Description of the Related Art

The use of porphyrin compounds, and in particular hematoporphyrin and its derivative mixture hematoporphyrin derivative (HPD), have been known for some time to be useful systemically when combined with irradiation, for the treatment and diagnosis of malignant cells. The porphyrins appear to "naturally" localize in malignant tissue where they absorb light at certain wavelengths when irradiated, providing a means to detect the tumor by the location of the fluorescence. Accordingly, preparations containing the porphyrins are useful in the diagnosis and detection of such tumor tissues. (See e.g. "Porphyrin Photosensitization", Kessel, D., et al., eds. (1983) Plenum Press). In addition, the porphyrins also have the capability of exhibiting a cytotoxic effect on the cells or other tissues in which they are localized when irradiated at the appropriate wavelength. (See, e.g., Diamond, I., et al., *Lancet* (1972) 2: 1175-1177; Dougherty, T. J. et al., "The Science of Photo Medicine" (1982) J. D. Regan & J. A. Parrish, eds., pp. 625-638; Dougherty, T. J., et al., "Cancer: Principles and Practice of Oncology" (1982) V. T. DeVita Jr., et al., eds., pp. 1836-1844). It has been postulated that the cytotoxic effect of the porphyrins is due to the formation of singlet oxygen upon irradiation (Weishaupt, K. R., et al., *Cancer Research*, (1976) 36: 2326-2329). The successful treatment of AIDS-related oral Kaposi's Sarcoma with a purified form of HPD, Photofrin® porfimer sodium, was described in Schweitzer, V. G. et al., *Otolaryngology—Head and Neck Surgery*, (1990) 102: 639-649.

In addition to systemic use for the treatment and diagnosis of tumors, the porphyrins can be used in a variety of other therapeutic applications. For example, photosensitizers are useful in the detection and treatment of artherosclerotic plaques as disclosed in U.S. Pat. Nos. 4,517,762 and 4,577,636. U.S. Pat. Nos. 4,500,507 and 4,485,806 describe the use of radiolabeled porphyrin compounds for tumor imaging. Porphyrin compounds have also been used topically to treat various skin diseases as disclosed in U.S. Pat. No. 4,753,958.

A number of porphyrin photosensitizer preparations have been disclosed for therapeutic applications. A photosensitizer preparation widely used in the early stages of photodynamic therapy both for detection and treatment was a crude derivative of hematoporphyrin, also called hematoporphyrin derivative (HPD) or Lipson derivative, prepared as described by Lipson et al., J. Natl. Cancer Inst. (1961) 26: 1-8. A purified form of the active component(s) of HPD was prepared by Dougherty and co-workers by adjustment of the pH to cause aggregation and recovery of the aggregate, as disclosed in U.S. Pat. Nos. 4,649,151, 4,866,168, 4,889,129 and 4,932,934. A purified form of this product has been used clinically under the trademark Photofrin® porfimer sodium (also referred to as polyhematoporphyrin ether/esters).

Porfimer sodium is prepared by following the method of Lipson as modified by Dougherty et al. In brief, hematoporphyrin is first treated with a mixture of sulfuric and acetic acids which produces a mixture of mono- and di-acetate of hematoporphyrin (Hp) and its dehydration products, hydroxyethylvinyldeutero porphyrin (Hvd) and protoporphyrin. This mixture upon treatment with 0.1 N NaOH undergoes hydrolysis and coupling to produce hematoporphyrin derivative (Hpd) which is a mixture of Hp, Hvd, protoporphyrin and a higher molecular weight fraction consisting of a mixture of porphyrin oligomers. In the Dougherty et al. disclosure, this higher molecular weight fraction was separated by adjustment of the pH to around 9.5 and removal of the resulting aggregate by membrane filtration. See U.S. Pat. No. 4,649,151.

The structure of porfimer sodium and the nature of linkages joining the porphyrin units has been the subject of discussion for quite some time. Bonnett and Berenbaum, Adv. Exp. Biol. Med. 160, 241 (1983) proposed that the structure of the tumor localizing component might be a dimer or oligomer linked by ether or carbon to carbon covalent bonds. Dougherty et al., Prog. Clin. Biol. Res., (1984) 170: 301-314, presented evidence from fast atom bombardment mass spectroscopy (FAB-MS) and NMR spectroscopy that the localizing components were most likely the isomers of dihematoporphyrin ether. Recently Kessel and coworkers, Cancer Res. 47, 4642 (1987) have suggested that the tumor localizing components of porfimer sodium might be porphyrin dimers with ester and ether linkages. However, the presence of a polymeric mixture was not ruled out. Recently it has been reported that hematoporphyrin dimer, trimer and their dehydration products with ether linkages are biologically active and are likely active components in porfimer sodium, Pandey et al., Tetrahedron Lett. 29: 4567 (1988). Hematoporphyrin dimer with ester linkage was found to be biologically inactive and is only a minor component of porfimer sodium, Pandey et al., Cancer Res. 49: (8) 2042-2047 (1989). It is now believed, from fast atom bombardment mass spectral analysis of porfimer sodium, that it is in fact a complex mixture of oligomers having from two up to eight porphyrin units linked together and that the porphyrin units are hematoporphyrin, hydroxyethylvinyl-deuteroporphyrin and protoporphyrin units. The porphyrin units are linked with ether and/or ester bonds as generally exemplified in structure I, below:

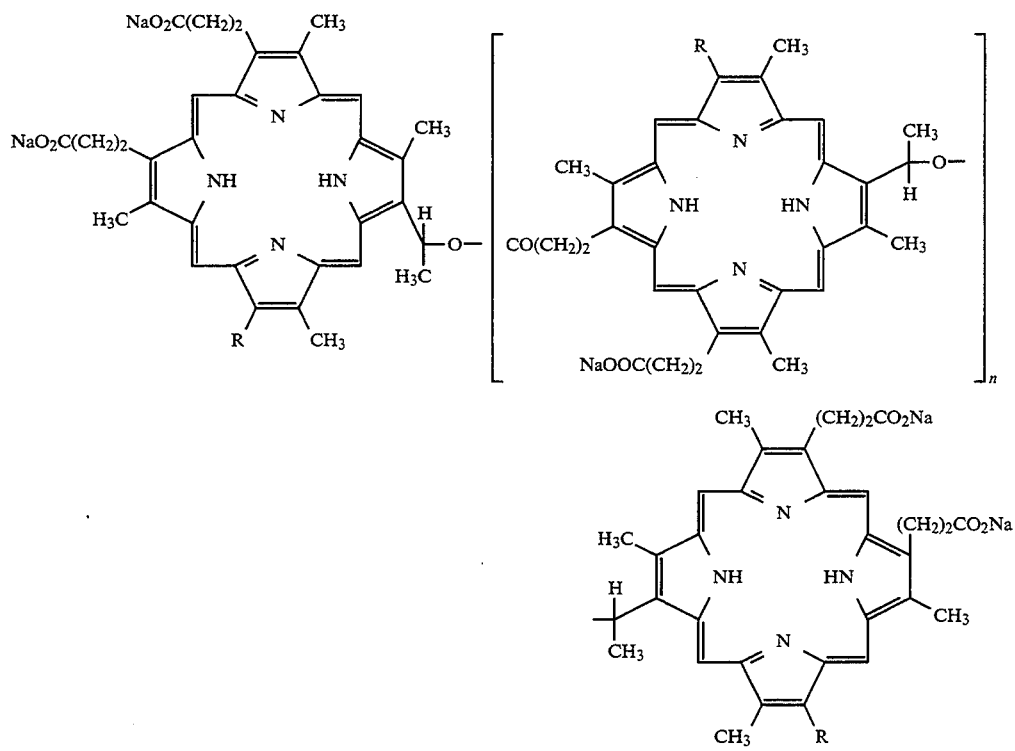

In the foregoing structures, n is an integer from 0 to 6 and R is hydroxyethyl or vinyl. It is understood that the composition includes a combination of oligomers of varying chain length, that is, a combination of compounds where n is 0, 1, 2, 3, 4, 5 or 6 (dimers, trimers, tetramers, etc.). In addition, the composition includes a combination of hematoporphyrin, hydroxyethylvinyldeuteroporphyrin, and protoporphyrin units (i.e. R is hydroxyethyl and/or vinyl).

The porphyrin units may be linked together in different ring orientations, depending on whether ether or ester bonds are involved. Referring to the structure below:

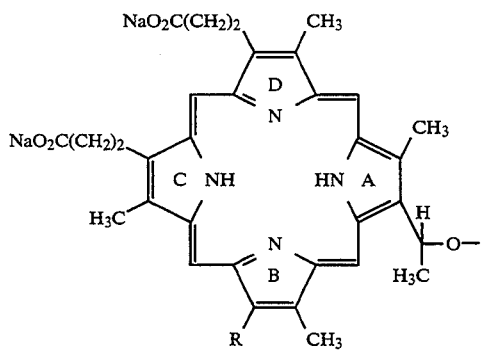

where the rings of the porphyrin are labelled A, B, C and D, the ether linked porphyrins may be joined only with A-A, A-B, B-A, or B-B orientations. Ester linked porphyrins may be joined with the A-C, A-D, B-C or B-D orientations.

Heretofore, the use of porfimer sodium as a therapeutic or diagnostic agent has been hindered by the relative instability of the product. Porfimer sodium prepared by the prior art process degrades rapidly when exposed to heat and is stable for only a few hours at room temperature. Accordingly, the solution is generally kept frozen and thawed immediately prior to use.

The use of such a frozen solution has many obvious disadvantages. Because it has to be kept frozen, it must be shipped and stored in a frozen state, necessitating the use of special freezing conditions. For example, the product must be shipped in special containers using dry ice or the like as a refrigerant. This is a major drawback, adding to the cost and logistics of using the product. At the point of use, the frozen solution must be stored at −20° C., which is below the operating temperatures of some freezers thereby necessitating special freezer equipment. In addition, the frozen product must undergo a thawing period and is therefore not useable immediately with a patient.

Various methods have been proposed to overcome that instability of the product. U.S. Pat. No. 5,059,619 discloses a stable, freeze-dried preparation of porfimer sodium which is obtained by freeze-drying an aqueous solution of the photosensitizer composition. This preparation is reconstituted prior to administration. Lai et al., U.S. Pat. No. 4,882,234, discloses a storage stable composition which is obtained by heat treating a buffered pH 5-9 aqueous solution of hematoporphyrin at a temperature of 60° C. to about 120° C. for 5-100 hours. The resulting product appears to have a different composition than porfimer sodium and is stated to contain at least 80% by weight of its porphyrins as ester linked oligomers where the oligomeric chain is an average of about 3 to 7.

It is an object of the present invention to provide porfimer sodium compositions which exhibit enhanced thermal and temporal stability as compared to preparations shown in the art, and which maintain high levels of activity as photodynamic therapeutic and diagnostic agents. It is a further object of this invention to provide processes for producing such materials and methods of using such materials.

SUMMARY OF THE INVENTION

It has been found that a composition of porfimer sodium which exhibits enhanced stability may be obtained by taking the product formed from the reaction of hematoporphyrin with acetic/sulfuric acid, (hereinafter referred to as "the acetylated hematoporphyrin composition"), and reacting it with alkali at such conditions to reduce the amount of porphyrin oligomers joined by ester linkages to less than 10%, preferably 4–5% (as shown by high performance liquid chromatography (HPLC) in conjunction with base hydrolysis). The resulting product has enhanced thermal and temporal stability and therefore a greater shelf-life.

The porfimer sodium compositions of the present invention may be defined as a biologically active composition being fluorescent, photosensitizing and having the capability of localizing in and being retained in tumor tissue as compared to normal tissues which composition comprises a mixture of porphyrin oligomers, said oligomers comprised of two to eight porphyrin molecules covalently linked by ether and ester bonds wherein at least one porphyrin molecule has the formula:

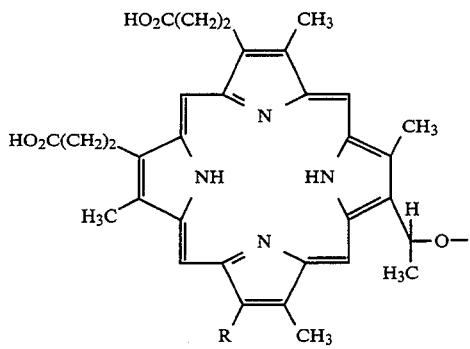

wherein R is hyroxyethyl or vinyl and wherein the bond shown forms said covalent linkage; and the pharmaceutically acceptable salts thereof; with the proviso that the percentage of ester linkages in said composition are less than 10% of the composition as shown by HPLC in conjunction with base hydrolysis.

The resulting porfimer sodium compositions of the present invention are characterized, as stated, in that they contain less than 10% of their oligomeric linkages as ester bonds as shown by base hydrolysis on HPLC assay. These compositions are prepared by employing processes which allow the ester oligomeric linkages to hydrolyze in the reaction process of the acetylated hematoporphyrin composition with alkali, leading to a higher percentage of ether linkages in the product. The ester content of porfimer sodium can be characterized by utilizing HPLC in conjunction with exhaustive base hydrolysis. In this procedure, the product is assayed before and after treatment with base which hydrolyzes the ester bonds. As stated, the product exhibits enhanced stability as compared to the composition of the prior art.

The present invention can therefore be described by the processes by which the porfimer sodium oligomer products are formed. Such a process includes the step of reacting the acetylated hematoporphyrin composition with alkali for sufficient time and temperature to hydrolyze the ester linkages of the oligomeric products formed such that there are less than 10% by weight ester-linked oligomers in the composition. Alternatively, the acetylated hematoporphyrin composition can be reacted with alkali, preferably sodium hydroxide, and the resulting product is held at an alkaline pH for sufficient time to hydrolyze the ester linkages.

In a preferred embodiment, the preparation process comprises the reaction of the acetylated hematoporphyrin composition with 0.1N–0.2N sodium hydroxide at room temperature for 16–24 hours. The pH of the solution is adjusted to 9.4–9.6 with hydrochloric acid and purified by diafiltration with a membrane filter to eliminate low molecular weight components.

In additional aspects, this invention provides compositions containing the predominantly ether linked oligomer compositions and their use in photodynamic therapy and diagnosis.

DETAILED DESCRIPTION

BRIEF DESCRIPTION OF THE DRAWINGS

In the specification and claims, reference will be made to the accompanying drawings in which:

FIG. 1 is a graph showing the stability of the compositions of the present invention over time at 2°–4° C. as compared to the composition of the art.

FIG. 2 is a graph showing the stability, over time at 4° C., of compositions prepared by reacting the acetylated hematoporphyrin composition with alkali for a period of 24 hours as compared with a composition of the art.

DESCRIPTION OF THE PREFERRED EMBODIMENTS

The starting material employed in the present invention is hematoporphyrin dihydrochloride. Hematoporphyrin dihydrochloride is derived from the naturally occurring compound, heme, and is available commercially from for example, Aldrich Chemical Company. The material is available in its protonated HCl salt form as a dry powder.

In accordance with the present invention, the hematoporphyrin dihydrochloride starting material is reacted with acetic acid/sulfuric acid as taught by Lipson et al., J. Natl. Cancer Inst. 26: 1–8 (1961) and Dougherty et al., U.S. Pat. No. 4,649,151 to produce the acetylated hematoporphyrin composition. This composition is then reacted with alkali, preferably 0.1N–0.2N sodium hydroxide, for sufficient time and at sufficient temperature to hydrolyze the ester linkages such that there is less than 10%, preferably less than 4–5% esters in the composition.

In one embodiment, the acetylated hematoporphyrin is reacted with 0.1N sodium hydroxide for at least an hour at room temperature. The solution is purified using room temperature diafiltration and stored at 4° C. from 14 to 21 days. The material is then repurified using a diafiltration procedure.

In an alternate procedure, the acetylated hematoporphyrin is dissolved in either 0.1N or 0.2N sodium hydroxide and allowed to react for 16 to 24 hours at room temperature. The solution is then purified using a room temperature diafiltration procedure or using a diafiltration procedure at 35°–40° C.

Using an additional method, the acetylated hematoporphyrin is dissolved in either 0.1N or 0.2N sodium hydroxide and allowed to react for one hour at 35°–45°

C. The solution is then purified at room temperature or at 35°–45° C. using a diafiltration procedure.

Alternatively, the acetylated hematoporphyrin is dissolved in 0.1N sodium hydroxide and allowed to react for one hour at room temperature. Additional sodium hydroxide is then added to a concentration of 0.2N and held there for 10–24 hours or a 1N concentration and held for 2 hours. The solution is then purified at room temperature using the diafiltration procedure.

In an alternative procedure, acetylated hematoporphyrin is dissolved in 0.1N sodium hydroxide and allowed to react for one hour at room temperature. The pH of the solution is adjusted to 9.6 with hydrochloric acid and the resulting mixture held for 3 days at room temperature.

The improvements over the Dougherty process in each of the aforementioned variations results in final solutions that are more stable, thus allowing storage in the liquid state at 1°–4° C. over an extended period of time.

At present, the preferred embodiment for preparing the stable porfimer sodium composition is to react the acetylated hematoporphyrin with 0.1N sodium hydroxide and allowing the reaction to occur for 16–24 hours. The solution is then purified by diafiltration at room temperature.

The solution of the acetylated hematoporphyrin composition is an aqueous solution. The aqueous alkali solution is generally in a concentration of 0.1N–0.2N, but concentrations of up to 1N may be used. Generally, the ratio of acetylated hematoporphyrin to alkali solution is 1:50.

The time and temperature for the reaction are related. Higher temperatures employ shorter times while lower temperatures require longer periods of time to hydrolyze the esters. The concentration of alkali is also related, in that stronger alkali concentrations require shorter reaction times. The temperature is generally moderate, from room temperature to temperatures of 40°–45° C. Higher temperatures are not preferred since degradation of the products tends to occur at higher temperatures. The time, temperature and strength of the alkali should be adequate to hydrolyze the ester bonds such that about 90% or greater of the oligomers are ether linked oligomers. This conversion can be monitored by such techniques as exhaustive base hydrolysis followed by HPLC (high performance liquid chromatography) analysis. Examples of times and temperatures which give the desired results are about 4° C. for 14–21 days, room temperature for 16–24 hours, 35°–45° C. for one hour, room temperature for one hour, adjustment of the pH to 9.6 and holding for 3 days, then purification at room temperature.

The oligomer product of the present invention can be characterized in terms of its chemical make-up and properties. Although not understood with certainty, it is believed that the product is a mixture of oligomers in which up to eight porphyrin units which are hematoporphyrin, hydroxyethylvinyldeuteroporphyrin and protoporphyrin units are covalently linked together by ether or ester bonds as described on page 4–5 of this application. It is a property of the present invention that no more than 10% of the composition consists of ester linked oligomers.

The product may be characterized by determining the ester content of the composition using HPLC in conjunction with exhaustive base hydrolysis. In this procedure, the product is assayed on HPLC to establish a baseline, then subjected to exhaustive treatment with base, such as 1N sodium hydroxide for 12–18 hours to hydrolyze all of the ester bonds. The resulting product is then assayed once more on HPLC. By comparing the HPLC chromatogram before and after base hydrolysis one can determine the percentage ester content in the original composition. As stated, it is a property of the claimed composition that it contains no more than 10% ester linked oligomers when analyzed using this procedure.

Without intending to be bound to any particular theory of how the present invention operates, it is now believed by the present inventors that the invention relies on a series of reactions to yield the composition of the invention. In the first reaction, the acetylated hematoporphyrin composition forms oligomeric linkages when reacted with alkali. Some of the oligomers formed are ether linkages and some are esters. If the reaction is allowed to continue for appropriate time and under appropriate conditions, the ester linkages hydrolyze and the resulting compositions formed is then predominantly ether linked oligomers which show enhanced stability.

As stated above, the compositions of the present invention show enhanced stability. Table 1 shows a comparison of the purity of the products produced by the prior art process disclosed by U.S. Pat. No. 4,649,151 ("the Dougherty process") versus three of the variations which include (a) keeping the reaction of the acetylated hematoporphyrin and 0.1N sodium hydroxide at room temperature for 24 hours followed by diafiltration at room temperature; (b) keeping the reaction of the acetylated hematoporphyrin and 0.1N sodium hydroxide for 1 hour at 40°–45° C.; or (c) keeping the reaction of the acetylated hematoporphyrin 15 and 0.1N sodium hydroxide at room temperature for 1 hour, adjusting the pH to 9.6 with 1N hydrochloric acid, holding for 3 days followed by diafiltration at room temperature. As is evident from looking at the data in Table 1, analysis of the resulting product in each case shows that over time while being stored at 2°–4° C. the product of the Dougherty Process degrades from 92% to 86% while the products obtained with each of the various improvements results in products with only minor degradation.

TABLE I

% Porfimer Sodium vs Storage Time at 2° C.–4° C.

| Storage Time (Days) | Dougherty Process | 24 Hour Hold | High Temperature | pH 9.6 3 Days |
|---|---|---|---|---|
| 0 | 92.1 | 90.8 | 92.9 | 91.0 |
| 1 | 90.3 | | | |
| 2 | 90.3 | | | |
| 4 | 89.8 | | | 91.0 |
| 6 | | 91.6 | | |
| 7 | 88.8 | | 93.3 | |
| 8 | | | | 91.3 |
| 9 | 87.9 | | | |
| 11 | 87.5 | | | |
| 14 | 87.2 | 90.6 | 92.8 | |
| 15 | | | | 92.6 |
| 18 | 86.5 | | | |
| 20 | | 89.4 | | |
| 21 | | | 92.0 | 92.0 |
| 23 | 86.0 | | | |
| 28 | 85.8 | 91.3 | 92.3 | 92.0 |
| 34 | | 90.2 | 92.4 | |

TABLE I-continued

| % Porfimer Sodium vs Storage Time at 2° C.–4° C. | | | | |
| --- | --- | --- | --- | --- |
| Storage Time (Days) | Dougherty Process | 24 Hour Hold | High Temperature | pH 9.6 3 Days |
| 49 | | 90.1 | | |

Dougherty Process: 0.1N NaOH 1 hour, purification at RT
24 Hour Hold: 0.1N NaOH 24 hours, purification at RT
High Temperature: 0.1N NaOH 1 hour at 40–45° C., purification at 40–45° C.
pH 9.6, 3 Day Hold: 0.1N NaOH 1 hour, pH to 9.6 w/1 NHCl, 3 day hold, purification at RT As further shown in FIG. 1, the product of the Dougherty Process has a constant loss of purity over time while each of the products obtained through the enhanced processes (a), (b) and (c) above shows enhanced stability at 2°–4° C.

As shown graphically in FIG. 2 the product obtained in each of several preparations using the preferred procedure of reacting the acetylated hematoporphyrin and 0.1N sodium hydroxide at room temperature for 24 hours followed by diafiltration at room temperature retains product stability over time versus product prepared by the Dougherty process.

The porfimer sodium oligomer product of this invention can be formulated into pharmaceutical preparations for injection. Such preparations can contain from 0.1 to about 3.0 grams per liter of the porfimer sodium material in a pharmaceutically acceptable nonpyrogenic aqueous injection vehicle. Typical preparations have pH's between about 7.0 and about 8.1 and are isotonic. They also are substantially free of any solid contaminants. The concentration, pH and ionic strength of the preparations can be adjusted by removing water by ultrafiltration, by adding liquids such as sterile water for injection, sterile saline for injection or bacteriostatic water for injection as these liquids are defined in the book *Remington's Pharmaceutical Sciences*, 1985, Mack Publishing Company, 1985, by adding pH adjusting materials such as U.S.P. sodium hydroxide or U.S.P. phosphoric acid, or the like. The pharmaceutical preparations are then packaged under sterile conditions in suitable vials, bottles, prefilled syringes, and the like for administration via intravenous infusion or intramuscular injection to patients.

The porfimer sodium oligomer products of the invention may be used in photodynamic therapy or diagnosis in the manner which is disclosed for such porphyrin based products. The amount of porfimer sodium oligomer product administered to the patent can range from about 0.1 mg to 10 mg per kilogram of body weight with dosages of 1 to 2 mg/kg being preferred.

The invention will now be further described with reference to the following Examples. These are presented solely to make clear preferred embodiments of the present invention and are not to be construed as limiting the scope of the invention which is as defined by the appended claims.

EXAMPLE 1

Acetylated hematoporphyrin (1 part by weight) is dissolved in 0.1N sodium hydroxide (50 parts by volume) and stirred for one hour at room temperature. After the stir period the solution is adjusted to pH 9.4 to 9.6 with 1N hydrochloric acid. It is filtered through a 5 μm filter and then concentrated to ¼(12.5 parts) of its original volume in an ultrafilter with 10,000 molecular weight cut off membranes. The solution is then purified via diafiltration maintaining constant volume with 120 volumes of water and keeping the pH at 9.4 to 9.6 with 0.1N sodium hydroxide. This is also done at room temperature. After the purification, the solution is removed from the ultrafilter, diluted to ⅜(18.8 parts) of its original volume and pH adjusted to 7.5 to 7.7 with 1N hydrochloric acid. The solution is then stored at 4° C. for 14 to 21 days. After storage, the solution is pH adjusted to 9.4 to 9.6 with 0.1N sodium hydroxide and concentrated to ¼(12.5 parts) of its original volume. The solution is then repurified as above. The solution is diluted to ⅜(18.8 parts) of its original volume and pH adjusted to 7.5 to 7.7 with 1N hydrochloric acid. The solution is then analyzed and, if necessary, it is adjusted to between 13 to 18 mg/mL by the addition of water. The solution is then filtered through a 0.22 μm filter into bottles for storage at 1° C. to 4° C. to await further processing.

EXAMPLE 2

Acetylated hematoporphyrin (1 part by weight) is dissolved in 0.1N or 0.2N sodium hydroxide (50 parts by volume) and stirred for 16 to 24 hours at room temperature. After the stir period the solution is adjusted to pH 9.4 to 9.6 with 1N hydrochloric acid. It is filtered through a 5 μm filter and then concentrated to ¼(12.5 parts) of its original volume in an ultrafilter with 10,000 molecular weight cut off membranes. The solution is then purified via diafiltration at room temperature or at 35° C. to 45° C., maintaining constant volume with 120 volumes of water and keeping the pH at 9.4 to 9.6 with 0.1N sodium hydroxide. After the purification, the solution is removed from the ultrafilter, diluted to ⅜(18.8 parts) of its original volume and pH adjusted to 7.5 to 7.7 with 1N hydrochloric acid. The solution is then analyzed and, if necessary, it is adjusted to between 13 to 18 mg/mL by the addition of water. The solution is then filtered through a 0.22 μm filter into bottles for storage at 1° C. to 4° C. to await further processing.

EXAMPLE 3

Acetylated hematoporphyrin (1 part by weight) is dissolved in 0.1N or 0.2N sodium hydroxide (50 parts by volume) and stirred for one hour at 35° to 45° C. After the stir period the solution is adjusted to pH 9.4 to 9.6 with 1N hydrochloric acid. It is filtered through a 5 μm filter and then concentrated to ¼(12.5 parts) of its original volume in an ultrafilter with 10,000 molecular weight cut off membranes. The solution is then purified via diafiltration at room temperature or at 35° to 45° C., maintaining constant volume with 120 volumes of water and keeping the pH at 9.4 to 9.6 with 0.1N sodium hydroxide. After the purification, the solution is removed from the ultrafilter, diluted to ⅜(18.8 parts) of its original volume and pH adjusted to 7.5 to 7.7 with 1N hydrochloric acid. The solution is then analyzed and, if necessary, it is adjusted to between 13 to 18 mg/mL by the addition of water. The solution is then filtered through a 0.22 μm filter into bottles for storage at 1° C. to 4° C. to await further processing.

EXAMPLE 4

Acetylated hematoporphyrin (1 Part by weight) is dissolved in 0.1N sodium hydroxide (50 parts by volume) and stirred for i hour at room temperature. Sodium hydroxide is then added to give an overall concentration (based on initial NaOH plus this addition) of either 1.1N (2 parts NaOH) or 0.2N (0.2 parts NaOH). This solution is then stirred for 2 hours (1.1N NaOH) or 24 hours (0.2N NaOH). After the stir period the solution is adjusted to pH 9.4 to 9.6 with 1N hydrochloric acid. It is then filtered through a 5 μm filter and then concentrated to ¼(12.5 parts) of its original volume in an ultrafilter with 10,000 molecular weight cut off membranes. The solution is then purified via diafiltration maintaining constant volume with 120 volumes of water and keeping the pH at 9.4 to 9.6 with 0.1N sodium hydroxide. This is also done at room temperature. After the purification, the solution is removed from the ultrafilter, diluted to ⅜(18.8 parts) of its original volume and pH adjusted to 7.5 to 7.7 with 1N hydrochloric acid. The solution is then analyzed and, if necessary, it is adjusted to between 13 to 18 mg/mL by the addition of water. The solution is then filtered through a 0.22 μm filter into bottles for storage at 1° C. to 4° C. to await further processing.

EXAMPLE 5

Acetylated hematoporphyrin (1 part by weight) is dissolved in 0.1N sodium hydroxide (50 parts by volume) and stirred for one hour at room temperature. After the stir period the solution is adjusted to pH 9.4 to 9.6 with 1N hydrochloric acid and is held at room temperature for 3 days. After the holding period, the solution is filtered through a 5 μm filter and then concentrated to ¼(12.5 parts) of its original volume in an ultrafilter with 10,000 molecular weight cut off membranes. The solution is then purified via diafiltration maintaining constant volume with 120 volumes of water and keeping the pH at 9.4 to 9.6 with 0.1N sodium hydroxide. This is also done at room temperature. After the purification, the solution is removed from the ultrafilter, diluted to ⅜(18.8 parts) of its original volume and pH adjusted to 7.5 to 7.7 with 1N hydrochloric acid. The solution is then analyzed and, if necessary, it is adjusted to between 13 to 18 mg/mL by the addition of water. The solution is then filtered through a 0.22 μm filter into bottles for storage at 1° C. to 4° C. to await further processing.

We claim:

1. A porfimer sodium pharmaceutical composition comprised of porphyrin oligomers having ether and ester covalent linkages wherein less than 10% of said linkages in the porphyrin oligomers are ester linkages, said oligomers in association with a pharmaceutically acceptable carrier.

2. A biologically active composition being fluorescent, photosensitizing and having the capability of localizing in and being retained in tumor tissue as compared to normal tissues which composition comprises a mixture of porphyrin oligomers, said oligomers comprised of two to eight porphyrin molecules covalently linked by ether and ester linkages wherein at least one porphyrin molecule has the formula:

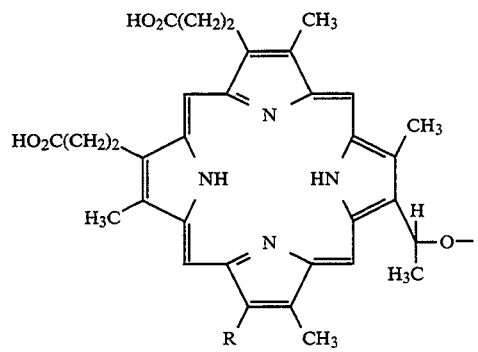

wherein R is hydroxyethyl or vinyl and wherein the bond shown forms said covalent linkage, and the pharmaceutically acceptable salts thereof; with the proviso that the percentage of said linkages which are ester linkages is less than 10% of said linkages.

3. A porfimer sodium pharmaceutical composition comprised of porphyrin oligomers having ether and ester covalent linkages wherein less than 10% of the linkages in the porphyrin oligomers are ester linkages, in association with a pharmaceutically acceptable carrier, wherein said porphyrin oligomers are prepared by a process which comprises treating acetylated hematoporphyrin under alkali concentration, time and temperature conditions sufficient to reduce the percentage of ester linkages in the porphyrin oligomers to less than 10% of the linkages in the oligomers.

4. The composition of claims 3 wherein the alkali concentration is in a range of 0.1N–1N.

5. The composition of claim 4 wherein the alkali is sodium hydroxide and the time and temperature conditions are 1 hour at room temperature followed by 4° C. for 14–21 days.

6. The composition of claim 4 wherein the alkali is sodium hydroxide and the time and temperature conditions are 16–24 hours at a temperature less than 45° C.

7. The composition of claim 3 wherein the alkali is sodium hydroxide, and the conditions are alkali concentration of 0.1N for 1 hour at room temperature followed by alkali concentration of 0.2N–1N for 2–4 hours at room temperature.

* * * * *

UNITED STATES PATENT AND TRADEMARK OFFICE
CERTIFICATE OF CORRECTION

PATENT NO. : 5,438,071
DATED : August 1, 1995
INVENTOR(S) : Steven L. Clauss, et al.

It is certified that error appears in the above-identified patent and that said Letters Patent is hereby corrected as shown below:

On the title page, item:

[73] Assignee: delete "American Cyanamid Company, Stamford, Conn" and insert therewith --Quadra Logic Technologies Inc., Vancouver, B.C., CANADA--.

Signed and Sealed this

Twelfth Day of December, 2000

Attest:

Q. TODD DICKINSON

Attesting Officer

Director of Patents and Trademarks